United States Patent
Byrd et al.

(10) Patent No.: US 8,509,916 B2
(45) Date of Patent: Aug. 13, 2013

(54) BILUMEN GUIDE CATHETERS FOR ACCESSING CARDIAC SITES

(75) Inventors: Charles L. Byrd, Fort Lauderdale, FL (US); Kenneth C. Gardeski, Plymouth, MN (US); Michael R. Leners, East Bethel, MN (US); Linda L. Lach, Vadnais Heights, MN (US); Ralph J. Thomas, Champlin, MN (US); Jesse T. Torbert, Cleveland Heights, OH (US); James F. Kelley, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 1103 days.

(21) Appl. No.: 10/319,245

(22) Filed: Dec. 16, 2002

(65) Prior Publication Data

US 2004/0116878 A1    Jun. 17, 2004

(51) Int. Cl.
*A61N 1/05* (2006.01)

(52) U.S. Cl.
USPC .......................................... 607/117; 604/263

(58) Field of Classification Search
USPC ......... 607/116, 119, 112; 600/585; 604/263, 604/523; 606/129
See application file for complete search history.

(56) References Cited

U.S. PATENT DOCUMENTS

| | | | |
|---|---|---|---|
| 4,602,645 A | 7/1986 | Barrington et al. | 128/786 |
| 5,120,323 A * | 6/1992 | Shockey et al. | 604/528 |
| 5,188,606 A * | 2/1993 | Maloney et al. | 604/161 |
| 5,246,014 A | 9/1993 | Williams et al. | |
| 5,304,218 A | 4/1994 | Alferness | |
| 5,374,245 A | 12/1994 | Mahurkar | 604/43 |
| 5,395,332 A * | 3/1995 | Ressemann et al. | 604/103.1 |
| 5,662,119 A | 9/1997 | Brennen et al. | |
| 5,792,116 A * | 8/1998 | Berg et al. | 604/202 |
| 5,827,229 A | 10/1998 | Auth et al. | 604/171 |
| 5,873,842 A | 2/1999 | Brennen et al. | |
| 5,897,584 A | 4/1999 | Herman | |
| 5,902,289 A * | 5/1999 | Swartz et al. | 604/530 |
| 5,902,331 A | 5/1999 | Bonner et al. | |
| 5,941,871 A * | 8/1999 | Adams et al. | 604/523 |
| 6,010,522 A * | 1/2000 | Barbut et al. | 606/200 |
| 6,033,414 A | 3/2000 | Tockman et al. | |
| 6,053,900 A * | 4/2000 | Brown et al. | 604/500 |
| 6,132,390 A | 10/2000 | Cookston et al. | |
| 6,132,456 A | 10/2000 | Sommer et al. | |

(Continued)

OTHER PUBLICATIONS

Arkema's Pebax homepage, http://www.pebax.com/sites/pebax/en/home.page, access Aug. 5, 2007.*

*Primary Examiner* — Niketa Patel
*Assistant Examiner* — Alyssa M Alter

(57) ABSTRACT

Bilumen catheters and methods of using same for facilitating implantation of cardiac leads for applying electrical stimulation to and/or sensing electrical activity of the heart through one or more electrode positioned at an implantation site within a heart chamber or cardiac vessel adjacent a heart chamber, and more particularly to a method and apparatus for introducing such a cardiac lead having low torqueability and pushability through a tortuous pathway to enable attachment of the cardiac lead at the implantation site employing a bilumen guide catheter are disclosed. The bilumen catheter body includes a relatively large diameter delivery lumen to introduce a small diameter cardiac lead and a small diameter guide lumen to receive a stylet or guidewire to locate the guide catheter body distal end at the implantation site. The small diameter lumen within a small diameter guide tube extends distally from the delivery exit port of the delivery lumen.

9 Claims, 11 Drawing Sheets

(56) References Cited

U.S. PATENT DOCUMENTS

| | | | |
|---|---|---|---|
| 6,146,338 A | 11/2000 | Gardeski et al. | |
| 6,152,909 A * | 11/2000 | Bagaoisan et al. | 604/523 |
| 6,159,195 A * | 12/2000 | Ha et al. | 604/500 |
| 6,185,464 B1 | 2/2001 | Bonner et al. | |
| 6,203,507 B1 * | 3/2001 | Wadsworth et al. | 600/585 |
| 6,234,951 B1 * | 5/2001 | Hastings | 600/3 |
| 6,254,611 B1 * | 7/2001 | Vrba | 606/108 |
| 6,270,465 B1 * | 8/2001 | Keith et al. | 600/585 |
| 6,280,433 B1 * | 8/2001 | McIvor et al. | 604/524 |
| 6,283,951 B1 * | 9/2001 | Flaherty et al. | 604/529 |
| 6,306,106 B1 * | 10/2001 | Boyle | 600/585 |
| 6,379,346 B1 | 4/2002 | McIvor et al. | |
| 6,494,846 B1 * | 12/2002 | Margolis | 600/585 |
| 6,508,777 B1 * | 1/2003 | Macoviak et al. | 604/4.01 |
| 6,585,642 B2 * | 7/2003 | Christopher | 600/156 |
| 6,758,836 B2 * | 7/2004 | Zawacki | 604/284 |
| 7,008,412 B2 * | 3/2006 | Maginot | 604/523 |
| 2002/0072710 A1 | 6/2002 | Stewart et al. | 604/164.02 |
| 2002/0077687 A1 * | 6/2002 | Ahn | 607/120 |
| 2003/0032936 A1 | 2/2003 | Lederman | |

* cited by examiner

BILUMEN GUIDE CATHETERS FOR ACCESSING CARDIAC SITES

FIELD OF THE INVENTION

The present invention relates to bilumen guide catheters for introduction and implantation of cardiac leads for applying electrical stimulation to and/or sensing electrical activity of the heart or the introduction of other medical instruments and materials into cardiac vessels.

BACKGROUND OF THE INVENTION

Implantable permanent and temporary medical electrical stimulation and/or sensing leads are well known in the fields of cardiac stimulation and monitoring, including cardiac pacing and cardioversion/defibrillation, and in other fields of electrical stimulation or monitoring of electrical signals or other physiologic parameters. In the field of cardiac stimulation and monitoring, the electrodes of epicardial or endocardial cardiac leads are affixed to the myocardium of the heart wall through either the epicardium or the endocardium, respectively, bear against the epicardium or endocardium, respectively, or are lodged in a coronary vessel.

The lead body of a permanent or temporary cardiac lead typically includes one or more insulated conductive wires surrounded by an insulating outer sheath. Each conductive wire couples a proximal lead connector element with a distal stimulation and/or sensing electrode. Temporary and permanent cardiac leads having a single stimulation and/or sensing electrode at the lead distal end, a single conductor, and a single connector element are referred to as unipolar cardiac leads. Temporary and permanent cardiac leads having two or more stimulation and/or sensing electrodes at the lead distal end, two or more respective conductors, and two or more respective connector elements are referred to as bipolar leads or multi-polar leads, respectively.

Epicardial or myocardial permanent and temporary cardiac leads, or simply epicardial leads, are implanted by exposure of the epicardium of the heart typically through a limited thorocotomy or a more extensive surgical exposure made to perform other corrective procedures. Endocardial permanent and temporary cardiac leads, or simply endocardial leads, are implanted through a transvenous route to locate one or more sensing and/or stimulation electrode along or at the distal end of the lead in a desired implantation site in a chamber of the heart or a blood vessel of the heart. It is necessary to accurately position the electrode surface against the endocardium or within the myocardium or coronary vessel at the implantation site.

Temporary epicardial or endocardial cardiac leads are designed to extend through the patient's skin to an external monitor or pacing pulse generator to provide temporary pacing and to be removed from the patient's body when temporary pacing is halted. Permanent epicardial and endocardial cardiac leads are designed to be coupled to a pacemaker or defibrillator implantable pulse generator (IPG) or an implanted monitor and to be chronically implanted in the patient's body. The proximal end of such permanent cardiac leads typically is formed with one or more lead connector element that connects to a terminal of the IPG or monitor.

Referring particularly to the transvenous implantation of permanent endocardial leads, the distal electrode of the endocardial cardiac lead is advanced through the subclavian, jugular, or cephalic vein and through the superior vena cava into the right atrium or right ventricle or into a cardiac vessel, e.g., the coronary sinus and vessels branching therefrom, so as to locate the distal electrode(s) at a desired implantation site. Such a pathway involves a number of twists and turns and is relatively tortuous. An active or passive fixation mechanism is incorporated into the distal end of the permanent endocardial lead and is deployed at the implantation site to maintain the distal end electrode in contact with the endocardium or within the myocardium.

Considerable effort has been undertaken to develop passive and active fixation mechanisms that are simple to use and reliable in maintaining the distal electrodes in position. Passive fixation mechanisms do not invade the myocardium but cooperate with cardiac tissue or structures to lodge the pace/sense electrode(s) against the endocardium. The most successful passive fixation mechanism includes a plurality of soft, pliant tines that bear against cardiac structure surfaces, e.g. the trabeculae in the right ventricle and the atrial appendage, to urge the distal tip electrode against the endocardium without penetrating into the myocardium. Active fixation mechanisms are designed to penetrate the endocardial surface and lodge in the myocardium without perforating through the epicardium or into an adjoining chamber. The most widely used active fixation mechanism employs a sharpened helix, which typically also constitutes the distal tip electrode. Typically, some sort of shroud or retraction mechanism is provided to shield the helix during the transvenous advancement into the desired heart chamber from which the helix can be advanced and rotated when the desired implantation site is reached to effect a penetrating, screw-in fixation. In one manner or another, the helix is adapted to be rotated by some means from the proximal end of the lead body outside the patient's body in order to screw the helix into the myocardium and permanently fix the electrode.

More recently, endocardial pacing and cardioversion/defibrillation leads have been developed that are adapted to be advanced into the coronary sinus to locate the distal electrode(s) adjacent to the left atrium or into coronary veins branching from the coronary sinus to locate the distal electrode(s) adjacent to the left ventricle. The distal end of such a coronary sinus lead is advanced through the superior vena cava, the right atrium, the valve of the coronary sinus, the coronary sinus, and, if employed to pace or sense the left ventricle, into a cardiac vein branching from the coronary sinus. Typically, coronary sinus leads employ a form of passive fixation, e.g., a preformed shape of the distal segment of the lead that relies on the close confinement within the vessel and column stiffness to maintain each electrode at a desired implantation site.

The heart beats approximately 100,000 times per day or over 30 million times a year, and each beat stresses at least the distal end segment of an implanted permanent endocardial lead. The lead conductors and insulation are subjected to cumulative mechanical stresses, as well as material reactions, over the years of implantation that can result in degradation of the insulation or fractures of the lead conductors with untoward effects on device performance and patient well being. The endocardial lead body is subjected to continuous flexing as the heart contracts and relaxes and is formed to be highly supple, flexible and durable. Thus, the permanent endocardial lead body lacks the column stiffness necessary to push the lead body through the twists and turns of the venous pathway and into the desired implantation sites in a right heart chamber or within the coronary sinus or cardiac vein. Historically, it has been necessary to temporarily stiffen the lead body to advance the lead distal end through these blood vessels and to locate the distal electrode(s) at the desired implantation site.

Implantable endocardial bipolar cardiac pacing leads of the type first disclosed in U.S. Pat. No. 3,348,548 included separate coiled wire conductors in a side-by-side configuration providing a coil lumen for receiving a stiffening stylet. Side-by-side coiled wire conductors have largely been supplanted by a coaxial configuration of the type shown in U.S. Pat. No. 3,788,329, wherein the separate coiled wire conductors are wound in differing diameters separated from one another by tubular insulating sheaths and extend coaxially about a central lumen for receiving the stiffening stylet. Other lead body configurations involving use of stranded wire conductors also are formed with a stylet lumen. Most current cardiac leads employ multi-filar, parallel-wound, coiled wire conductors electrically connected in common in an electrically redundant fashion as a single polarity lead conductor in each of the unipolar, bipolar and multi-polar lead configurations. Such redundant coiled wire conductors of bipolar and multi-polar lead bodies are coaxially arranged about the stiffening stylet receiving lumen and insulated from one another by coaxially arranged insulating sheaths separating each coiled wire conductor from the adjacent coiled wire conductor(s). The stiffening stylet is advanced through a proximal connector pin opening into the lead body lumen to stiffen the lead body during the transvenous introduction.

The stiffening stylet is typically provided with an enlarged diameter stylet knob or handle that can be grasped and rotated to impart torque to the lead distal end to steer the lead distal end around turns in the transvenous pathway. A variety of other torque tools for imparting torque to a stylet alone or to the stylet and lead body are disclosed in U.S. Pat. Nos. 6,033,414, 6,132,390, 4,624,266 and 4,422,460.

Frequently, two or more cardiac leads are introduced transvenously through the venous system into the right heart chambers or coronary sinus of the heart during initial implantation or in the replacement of previously implanted cardiac leads. Atrial and ventricular pacing leads have long been implanted to locate atrial pace/sense electrode(s) in the right atrium (RA) and ventricular pacing leads in the right ventricle (RV). Typically, the ventricular lead body is straight so that the ventricular pace/sense electrode can be directed from the superior vena cava (SVC) through the tricuspid valve and into the RV appendage employing a stiffening stylet. The atrial lead body is formed to assume a J-shape so that the atrial pace/sense electrode is directed toward and into the RA appendage upon entry into the RA from the SVC. The J-shape is straightened for advancement through the transvenous path using a straight stiffening stylet or by confining the RA lead body in a guide catheter sheath.

Many approaches have been explored to simplify and facilitate implantation of the atrial and ventricular leads simultaneously. One approach disclosed in U.S. Pat. No. 4,602,645 includes a bilumen guide catheter having RA and RV lead delivery lumens disposed side-by-side and extending between RA and RV lead delivery lumen entry and exit ports. The RA lead delivery lumen exit port is located proximally to the RV lead delivery lumen exit port to facilitate the introduction of the RA lead and the assumption of the J-shape as the RA lead is advanced into the RA from the RA delivery lumen exit port. The RV lead delivery lumen is larger in diameter or the same diameter as the RA lead delivery lumen, depending on the diameters of the RA and RV lead bodies.

Moreover, a number of multi-polar, cardiac leads have been designed to accommodate more than two electrodes or to make electrical connection with other components, e.g., blood pressure sensors, temperature sensors, pH sensors, or the like, in the distal portion of the lead. The increased number of separate polarity coiled wire conductors is difficult to accommodate in the conventional coaxial coiled wire conductor winding arrangement employing tubular insulating sheaths to separate the coil wire conductors of differing diameters having a desired overall lead body outer diameter. It has long been desired to minimize the diameter of the transvenous cardiac lead body in order to facilitate the introduction of several cardiac leads from the IPG through the same transvenous pathway.

The complexity of the leads, the number of leads implanted in a common path, and the advancement of coronary sinus leads deep in a coronary vein have led to efforts to at least not increase and optimally to decrease the overall diameter of the cardiac lead body without sacrificing reliability and usability. More recently, it has been proposed to diminish the lead body further by eliminating the lumen for receiving the stiffening stylet and by reducing the gauge and coil diameter of the coiled wire conductor or replacing it with highly conductive stranded filament wires or cables. In bipolar or multi-polar leads, each such cable extends through a separate lumen of the lead body to maintain electrical isolation.

Over the last 30 years, it has become possible to reduce endocardial lead body diameters from 10 to 12 French (3.3 to 4.0 mm) down to 2 French (0.66 mm) presently through a variety of improvements in conductor and insulator materials and manufacturing techniques. The lead bodies of such small diameter, 2 French, endocardial leads must possess little if any column strength that could cause the lead distal end fixation mechanism and electrode to perforate through the myocardium during implantation and if the lead body were to become axially force-loaded during chronic implantation. As a result, the small diameter lead bodies lack "pushability", that is the ability to advance the lead distal end axially when the lead proximal end is pushed axially, particularly when the lead body extends through the tortuous transvenous pathway.

Such small diameter endocardial leads then require distal fixation to maintain the electrode(s) at the desired implantation site. Active fixation helices that extend axially in alignment with the lead body to a sharpened distal tip and that have a helix diameter substantially equal to the lead body diameter are preferred because the fixation mechanism does not necessarily increase the overall diameter of the endocardial lead and is relatively robust, once the helix is screwed into the myocardium. Typically, but not necessarily, the fixation helix is electrically connected to a lead conductor and functions as a pace/sense electrode. In some cases, the lead body encloses one or more helical coiled or stranded wire conductor and lacks a lumen.

The lead bodies of such small diameter endocardial screw-in leads are so supple and flexible that it is difficult to rotate the lead distal end by application of rotary torque to the lead proximal end unless the lead body remains relatively straight and not confined by contact with vessel walls. This diminished "torqueability" prevents the rotation of the fixation helix at the lead distal end or renders the rotation unreliable once the lead body is advanced through a tortuous pathway and confined by contact against the vessel walls. To the degree that rotation torque can be transmitted from the lead proximal end to the lead distal end, the active fixation helix at the lead distal end can be over-rotated and screwed through the myocardium or under-rotated and not screwed into the myocardium sufficiently. Thus, it has been found necessary to use implantation instruments or tools that compensate for the lack of pushability and torqueability of the lead body.

In one approach, the lead body is enclosed within the lumen of a further sheath or introducer, and the lead and introducer are disposed within the lumen of the guide catheter. The fixation helix is located within the catheter lumen during advancement of the lead distal end fixation helix through the transvenous pathway and heart chamber or coronary vessel to dispose the fixation helix near the implantation site.

In commonly assigned U.S. Pat. No. 5,246,014, the introducer distal end and the lead distal end are configured to interlock or engage one another. The catheter, introducer and sheath lead body are advanced together through the transvenous, tortuous pathway to locate the fixation helix near the implantation site in the right atrium, right ventricle, coronary sinus, or cardiac vein. The fixation helix is pushed out of the catheter lumen distal end and the introducer catheter is rotated to screw the fixation helix into the myocardium by pushing and rotating the introducer proximal end extending proximally out of the catheter lumen outside the patient's body. In this approach, the inner introducer extends, in use, all the way to the catheter body distal end. Thus, the catheter distal segment is stiffened and may be difficult to advance through the tortuous pathway. Certain embodiments of the interlocking mechanism also increase the diameter of the lead distal end.

In further commonly assigned U.S. Pat. No. 6,408,214, the inner introducer, referred to as an inner sheath, and the outer catheter, referred to as an outer sheath each have preformed curves formed in distal sheath segments so that multiple curves can be induced as the inner and outer sheaths are axially adjusted relative to one another. The materials and dimensions of the inner and outer sheaths are selected to provide pushability and torqueablity of the assembly with the small diameter lead body disposed in the inner sheath lumen. The inner sheath is longer than the outer sheath, so that the inner sheath can be selectively moved out of the outer sheath lumen to advance a distal tip of the inner sheath to the implantation site. Again, the fixation helix is pushed out of the catheter lumen distal end and then rotated to screw the fixation helix into the myocardium by pushing and rotating the introducer proximal end extending proximally out of the catheter lumen outside the patient's body.

A further technique of implantation of such miniaturized endocardial screw-in leads disclosed in commonly assigned U.S. Pat. No. 5,897,584 employs a flexible guide catheter having a catheter body that has sufficient pushability and resistance to kinking that the guide catheter can be advanced through the transvenous pathway. The lead body is inserted into a catheter lumen during advancement of the catheter body distal end and fixation helix to the implantation site. Then, it is necessary to rotate the fixation helix from the proximal end of the assembly to screw the fixation helix into the myocardium at the implantation site. The distal advancement and rotation of the fixation helix is facilitated by a torque transfer device that is temporarily fitted over a proximal segment of the lead body extending proximally outside of the guide catheter hub and at a distance therefrom corresponding to or a fraction of the distance that the fixation helix is to be advanced distally for rotation into the myocardium.

Commonly assigned U.S. Pat. Nos. 6,280,433 and 6,379,346 disclose steerable catheters that are employed to access a blood vessel through a percutaneous incision and to be advanced to a site within the vascular system or a heart chamber. A bilumen catheter body is disclosed that includes a relatively large diameter delivery lumen and a smaller diameter stylet lumen that is blocked at a distal. The deflection mechanism in this case includes a stiffening stylet that can be selectively introduced into and removed from the stylet lumen from a proximal hub or handle. The stiffening stylet is advanced distally until the stylet distal end abuts the closed stylet lumen distal end to stiffen the catheter body to aid its introduction and advancement. The stylet distal end can be shaped when outside the stylet lumen opening to impart a curve to the catheter body when inserted into the lumen to assist in steering the catheter body distal end through the pathway. The stylet lumen is preferably lined with a wire coil sheath, and the handle and delivery lumen are preferably slittable by a slitting tool to aid in removing the introducer catheter from an electrical medical lead introduced through the delivery lumen. The delivery lumen exit port and the closed end of the stylet lumen are both located at the bilumen catheter body distal end.

A still further technique of implantation of such miniaturized, highly flexible, endocardial screw-in leads involves the use of a guidewire that is first advanced through the tortuous transvenous pathway. The endocardial lead is then advanced through the pathway alongside or over the guidewire as disclosed in U.S. Pat. Nos. 5,003,990, 5,304,218, 5,902,331, 6,132,456, and 6,185,464, for example. Some of these techniques require that the lead body be configured to provide an over-the-wire connection and possess sufficient column strength to be advanced over the guidewire. Other techniques employ elongated pusher tools that have sufficient column strength applied against the lead body distal end and extending alongside the lead body and the over the guidewire. These techniques are relatively complex to execute. Moreover, the rotation of the active fixation helix at the lead distal end through rotation of the assembly can still be problematic.

Thus, a need remains for an introducer system for a small diameter cardiac lead lacking pushability and torqueability that enables advancement of the distal electrode through tortuous pathways into a wide variety of implantation sites in a heart chamber or in a coronary vessel of the left heart chambers and reliable fixation at the selected implantation site.

Preferably, such a lead introducer system would also be of use in accessing cardiac sites for introducing medical instruments and materials or for implanting small diameter leads through other tortuous pathways of the body.

SUMMARY OF THE INVENTION

The present invention provides a bilumen guide catheter that can be employed to introduce and locate an electrode of a cardiac lead at a desired implantation site in a heart chamber or cardiac blood vessel or that can be employed to introduce medical instruments and materials into cardiac vessels that satisfies these needs. The bilumen guide catheter includes a relatively large diameter delivery lumen and a relatively small diameter guide lumen, wherein the guide lumen extends distally beyond a delivery lumen exit port. The bilumen guide catheter can be advantageously employed to introduce other electrical medical leads, materials and instruments through other tortuous pathways of the body.

In one preferred embodiment, the delivery lumen is adapted to receive and introduce a cardiac lead having a lead body enclosing a lead conductor and extending between a proximal lead connector element and a distal electrode through a tortuous pathway to the heart. Such a lead body may have insufficient pushability and torqueability to be easily advanced by itself through the tortuous pathway to locate the distal electrode at a desired implantation site. The bilumen catheter is adapted to be advanced through the tortuous pathway from outside the patient's body to the implantation site employing a guide tool introduced through or within the relatively small diameter guide lumen.

The guide tool includes one of a guidewire that has already been advanced through the tortuous pathway and a removable stiffening stylet that can be manually shaped to impart a bend in the distal segment of the guide catheter and can be inserted or withdrawn from the guide lumen. Further instruments or diagnostic fluids can be selectively advanced through the delivery lumen and/or the guide lumen to facilitate identification or advancement of the catheter body distal end to the implantation site preceding the advancement of the cardiac lead through the delivery lumen.

The bilumen guide catheter includes an elongated, bilumen catheter body having a catheter body proximal end coupled to a handle or hub and extending to a catheter body distal end. The guide lumen extends between a guide lumen entry port at the hub and a guide lumen exit port or closed distal end at the catheter body distal end. The delivery lumen extends between a delivery lumen entry port at the hub and a delivery lumen exit port proximal to the catheter body distal end. The bilumen catheter body is truncated at a point proximal to the catheter body distal end to terminate the delivery lumen and expose the delivery lumen exit port. The guide lumen and the delivery lumen extend in side-by-side relation within the bilumen catheter body distally from the hub to the respective guidewire and lead delivery exit ports.

The catheter body is reduced in diameter and stiffness in the distal segment extending between the delivery lumen exit port and the guide lumen exit port at the catheter body distal end, also referred to herein as a "leader". Consequently, the small diameter distal leader can be advanced readily over a guidewire or guided by a stylet inserted into the guide lumen through twists and turns of the tortuous pathway and thereby guides the advance of the larger diameter proximal segment of the catheter body. The small diameter distal leader can also be advanced deeply into narrow pathways or passages to dispose the more proximal delivery lumen exit port at a desired implantation site.

The bilumen catheter body can advantageously be formed by extrusion of a single polymeric material without the necessity of reinforcement or changing material characteristics along the length of the bilumen catheter body or by co-extrusion of a first tube defining the delivery lumen having a first durometer and a second tube defining the guide lumen of a second durometer and adhering the first and second tubes together. The distal leader can be shaped by removal of a distal segment of the first tube to form the delivery lumen exit port leaving the distal leader and guide lumen extending to the catheter body distal end.

Preferably, the delivery and guide lumen surfaces are coated with a lubricant to facilitate advancement of a cardiac lead or other instrument through the delivery lumen and a guidewire or stylet wire or other instrument through the guide lumen. The exterior surface of a distal portion of the bilumen catheter body including the distal leader can also be coated with the lubricant to facilitate advancement of the leader through the tortuous pathway.

The hub coupled to the guide catheter proximal end is advantageously formed with a hub delivery lumen axially aligned with the catheter body delivery lumen and a hub guide lumen axially aligned with the catheter body guide lumen. The hub and the catheter body are formed to be slittable along the lengths thereof to exposed the aligned hub and delivery lumen to release the cardiac lead introduced through the delivery lumen to a site of implantation.

The guide lumen exit port can be left open to provide for use either with a guidewire in an over-the-wire introduction or with a removable stiffening stylet. Alternatively, the guide lumen exit port can be closed for use with a removable stiffening stylet. The stiffening stylet can be provided with a selectable shape to enable advancement through the tortuous pathway or disposition of the delivery lumen exit port and at a selected implantation site. Or, a steerable stylet having a distal segment in which a bend can be selectively imparted or removed by manipulation of a proximal handle can advantageously be employed to impart a bend in the distal leader of the catheter body to steer the distal leader through bends and turns of a tortuous pathway.

The bilumen guide catheter having an open guide lumen exit port can advantageously be used to perform other functions, e.g., to facilitate blocking of a cardiac vessel employing a balloon catheter so that radiopaque diagnostic fluid can be introduced into the cardiac vessel to visualize the cardiac vessel in an angiographic procedure in order to identify a suitable implantation site.

The bilumen guide catheter and methods of the present invention advantageously simplify introduction of cardiac leads that lack a lumen for receiving a stiffening stylet and lack sufficient column strength to be pushed to a desired implantation site. The implantation sites include any selected implantation sites of the right atrium, the right ventricle, the coronary sinus, and the cardiac veins descending from the coronary sinus accessed through a transvenous pathway.

This summary of the invention and the advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

Other advantages and features of the present invention will be readily appreciated as the same becomes better understood by reference to the following detailed description when considered in connection with the accompanying drawings, in which like reference numerals designate like parts throughout the figures thereof and wherein.

Figure 1:
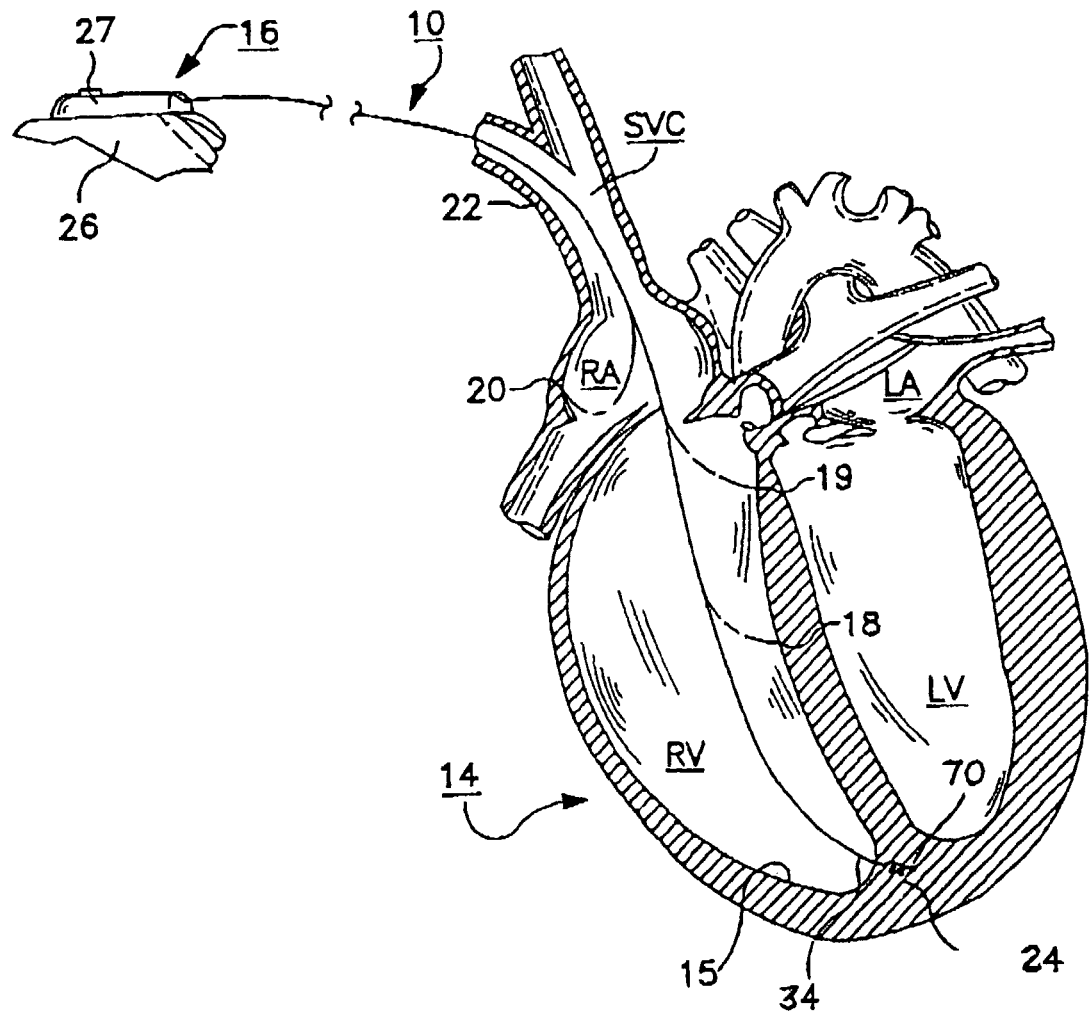
FIG. 1 is a schematic representation of a right heart cardiac lead bearing at least one cardiac electrode introduced into one of several illustrated implantation sites of the right heart chambers and coupled at the proximal lead connector end to an implantable medical device.

The drawing figures are not necessarily to scale.

DETAILED DESCRIPTION OF THE PREFERRED EMBODIMENTS OF THE INVENTION

In the following detailed description, references are made to illustrative embodiments for carrying out the invention. It is understood that other embodiments may be utilized without departing from the scope of the invention. The invention and its preferred embodiments may be employed in implantation of unipolar, bipolar or multi-polar, endocardial, cardiac pacing or monitoring leads having one or more pace/sense electrode(s) or sense electrode(s), respectively, at or adjacent the distal lead end. Similarly, the invention and its preferred embodiments may be implemented in the implantation of cardiac defibrillation/cardioversion leads including at least one cardioversion/defibrillation electrode and optionally including one or more pace/sense electrode(s) at or adjacent the distal lead end. Moreover, other sensors for sensing a physiologic parameter may be incorporated into the lead body. Each such pace/sense electrode, sense electrode, cardioversion/defibrillation electrode and sensor is coupled with an insulated electrical conductor extending proximally through the lead body to a lead proximal end connector assembly. The proximal connector end assembly is adapted to be coupled to the connector assembly of an external medical device, including an external pacemaker or monitor, or an implantable medical device, including an IPG for pacing, cardioversion/defibrillation or both or an implantable monitor. Therefore, it will be understood that the arrangement for introduction of a cardiac lead of the present invention can be employed to introduce permanently implantable and temporary cardiac leads of any of these types.

The arrangement of the present invention is particularly useful in introducing such small diameter cardiac leads that are devoid of a stylet lumen and are so flexible and possess such low column strength, pushability and torqueability that the lead distal end cannot be advanced transvenously and positioned at the desired implantation site without assistance. Moreover, one particular use of the arrangement of the present invention is to introduce such cardiac leads that are formed using stranded wire conductor(s) within a lead body diameter of about 0.010-0.026 inches of the type described in the above-incorporated, commonly assigned, '014 patent. The lead body outer diameter is minimized by use of such conductors and by eliminating the lumen for receiving a stiffening stylet. However, the arrangement of the present invention can also be employed to introduce cardiac leads that employ coiled wire conductors with or without a lumen for receiving a stiffening stylet. In the latter case, the stiffening stylet need not be used to achieve the introduction.

Figure 2:
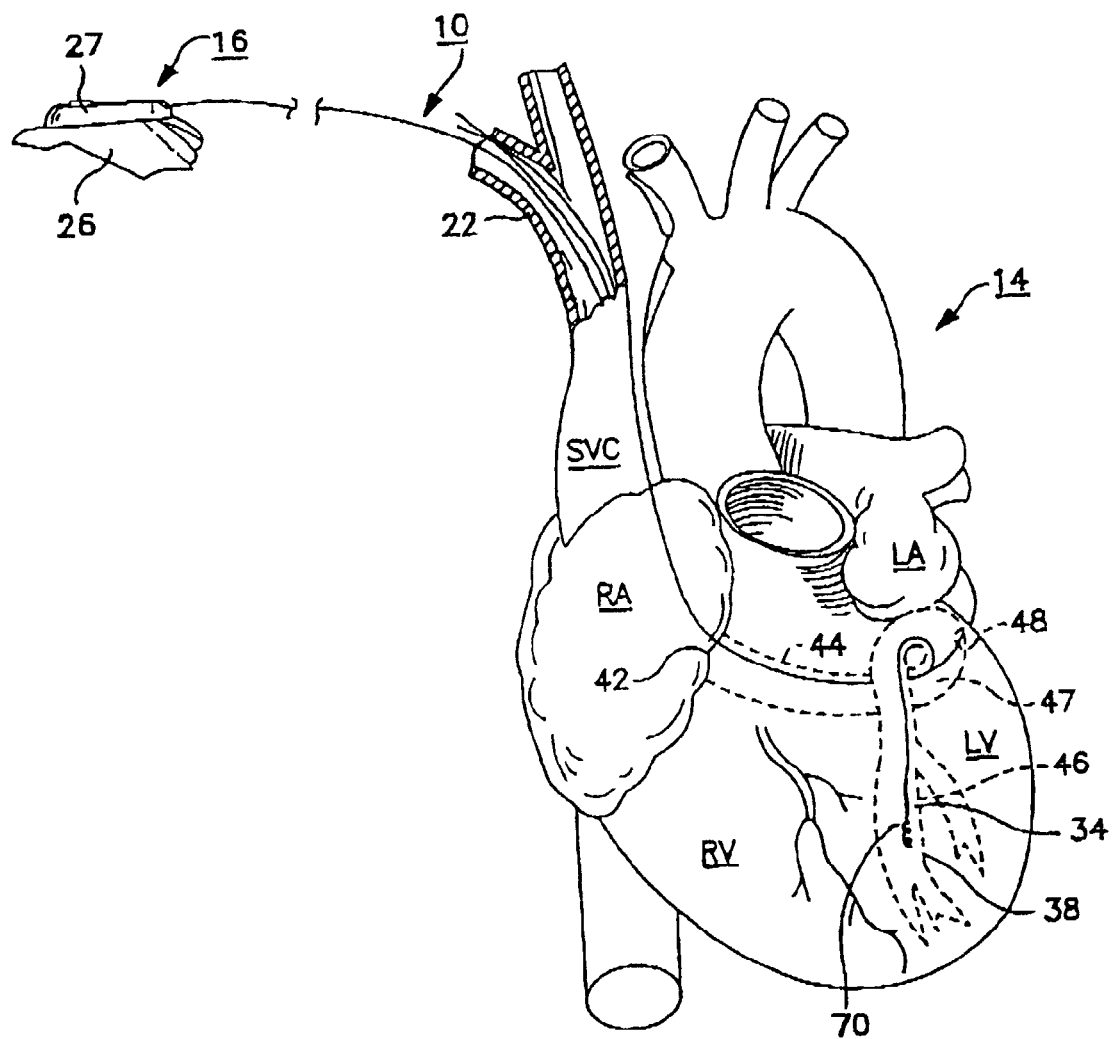
FIG. 2 is a schematic representation of a coronary sinus cardiac lead bearing at least one cardiac electrode introduced into one possible implantation sites within a cardiac vein adjacent to a left heart chamber and coupled at the proximal lead connector end to an implantable medical device.

FIGS. 1 and 2 are schematic representations of a cardiac lead 10 introduced into implantation sites of the right heart or the coronary vessels branching from the coronary sinus (CS). The cardiac leads 10 are introduced to the implantation sites in the cardiac blood vessels or chambers of the heart 14 through a tortuous pathway from a skin incision and venotomy made through the venous system, e.g., the right or left cephalic vein, other subclavian branches or the external or internal jugular vein in a manner well known in the art.

The proximal lead connector elements are schematically illustrated coupled in each instance to an implantable medical device (IMD) 16 of any of the above noted types. In FIGS. 1 and 2, heart 14 includes the upper heart chambers, the right atrium (RA) and left atrium (LA), and the lower heart chambers, the right ventricle (RV), and the left ventricle (LV). The coronary sinus (CS) is also depicted schematically in FIG. 2 extending from the opening 42 in the RA and extending laterally around the atria as the cardiac vein 44 and into the anterior interventricular vein 46 descending inferiorly along the LV.

The IMD 16 (depicted partially), which is implanted subcutaneously, i.e., below the skin, after IMD 16 is connected to the lead connector element(s), includes electronic components and a power supply enclosed with a housing 26 and a connector block 27. Connector block 27 has one or more bores for receiving the proximal lead connector element(s) of the cardiac lead 10 introduced into a right heart chamber or the CS. These figures illustrate some of the possible implantation sites and routes of introduction of cardiac electrodes on cardiac lead 10 to the implantation sites in accordance with the method and apparatus of the present invention. It will be understood that the illustrated right heart and CS cardiac leads 10 may be implanted at the implantation sites in the heart 14 and coupled to the connector block 27 of a suitable IMD 16. The illustrated cardiac lead 10 can have a unipolar, bipolar or multi-polar configuration and can be fabricated with pace/sense and/or cardioversion/defibrillation electrodes. Alternatively, the cardiac lead 10 can simply bear EGM sensing electrodes and/or physiologic sensors. The present invention is related to introduction arrangement and methods for introducing a cardiac electrode and/or physiologic sensor to one of the illustrated sites and other suitable implantation sites.

For simplicity, a unipolar right heart cardiac lead 10 is shown in FIG. 1 extending through the superior vena cava (SVC) 22 inferiorly through the RA and RV and lodging a distal electrode 34 and fixation helix 70 into the implantation site 24 in the RV apex of the heart 14. The cardiac lead 10 is formed having an elongated lead body extending between a connector element at a lead body proximal end (depicted inserted within a bore of the IMD connector block 27) and the distal fixation helix 70 extending distally from the lead body distal end. An electrode 34 is also supported at or adjacent to the lead body distal end, and a lead conductor extends within the lead body between the connector element and the electrode 34. The distal cardiac electrode 34 can be combined with the distal fixation helix 70 or be located along the lead body proximal to the fixation helix 70. Thus, the distal cardiac electrode 34 can be at or adjacent to (i.e., contiguous to) the lead body distal end.

In FIG. 1, the distal fixation helix 70 is adapted to be screwed into the myocardium and provide active fixation therewith through use of the introduction arrangement and method of the present invention as described hereafter. For example, FIG. 1 illustrates that the fixation helix 70 can be affixed at an implantation site 24 deep in the RV apex or in other implantation sites 19 and 18 in the septum between the RV and LV chambers when the lead 10 is implanted in the RV. The fixation helix 70 can alternatively be implanted in the RA with the fixation helix 70 screwed into an implantation site 20 of relatively thicker areas of the RA, e.g., the exterior right atrial wall or the right atrial appendage. It will also be understood that the fixation helix 70 can also simply attach the distal end of the cardiac lead 10 to the depicted implantation sites 18, 19 and 24 of the RV and the implantation site 20 of the RA (or other selected implantation sites of the RA and RV) and a separate cardiac electrode 34 can be provided on the lead body.

FIG. 2 illustrates the introduction of the cardiac lead 10 through the SVC and RA chamber and the ostium of the CS to extend alongside the LA chamber and the LV. The distal electrode(s) 34 can be located as depicted deep within the anterior interventricular vein 46 at LV implantation site 38 adjacent to the LV for LV stimulation and/or sensing applications. The distal CS electrode(s) can be located in the cardiac vein 47 at an implantation site 48 adjacent to the LA to provide LA stimulation and/or sensing applications. The distal fixation helix 70 is adapted to be screwed into the coronary vessel wall at the implantation site 38, 48 or other site within the coronary vessels and provide active fixation therewith through use of the introduction arrangement and method of the present invention as described hereafter.

Figure 3:
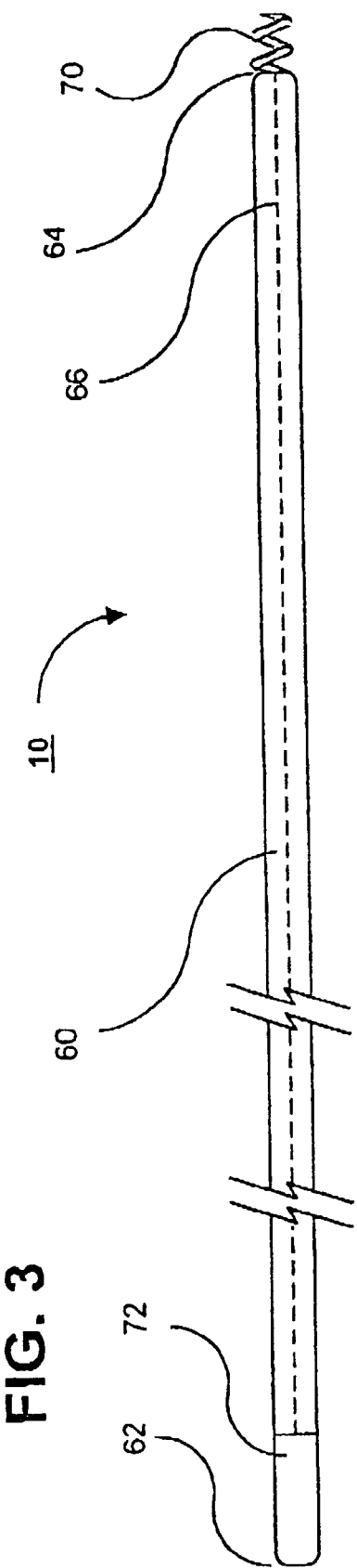
FIG. 3 is a plan view of an exemplary cardiac lead usable as a right heart cardiac lead or coronary sinus lead implanted at any of the implantation sites illustrated, for example, in FIGS. 1 and 2 employing the over-the-wire guide catheters of the present invention.
Figure 4:
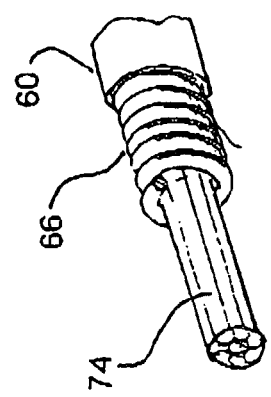
FIG. 4 is an expanded detail view of the construction of the lead body of the cardiac lead of FIG. 3.

An exemplary unipolar cardiac lead 10 that can be implanted in the sites depicted in FIGS. 1 and 2 is depicted in FIGS. 3 and 4. The cardiac lead 10 includes an elongated lead body 60 extending between a connector element 72 at a lead body proximal end 62 and a fixation helix 70 at the lead body distal end 64. The fixation helix 70 includes the electrode 34 in this illustrated example, and a lead conductor 66 extends within the lead body 60 between the connector element 72 and the distal fixation helix 70. The cardiac lead 10 is depicted in FIG. 3 having a lead proximal segment LPS, a lead intermediate segment LIS, and a lead distal segment LDS including the distal fixation helix 70 having a helix length HL.

The bilumen guide catheters of the present invention enable the implantation of a small diameter lead body 60 in the range of 1 French (0.33 mm) to 3 French (1.00 mm), but it will be understood that the over-the-wire guide catheters can be sized to facilitate implantation of larger diameter lead bodies exceeding 3 French in diameter. The lead body 60 can be formed in a variety of ways, and one example is depicted in FIG. 4. The illustrated exemplary lead body 60 includes a single-filar or multi-filar helical conductor 66 that is wound about a flexible conductive cable or a non-conductive tensile fiber 74 that is mechanically attached to the proximal and distal lead body ends 62 and 64. The cable or fiber 74 provides tensile strength to the lead body 60. However, the lead body 60 is highly flexible and does not possess column strength sufficient to push the fixation helix through the tortuous pathways illustrated in FIGs. and 2 or torqueability sufficient to rotate the fixation helix 70 into the myocardium or vessel wall by rotating the lead proximal segment LPS from the incision outside the patient's body.

It will be understood that the bilumen guide catheters and methods of use disclosed herein can be employed to introduce and secure any form of distal fixation hooks or fixation helices either extending distally like distal fixation helix 70 or laterally from the lead body in the manner of those distal fixation helices disclosed in U.S. Pat. Nos. 3,835,864 and 4,233,992, for example.

Figure 5:
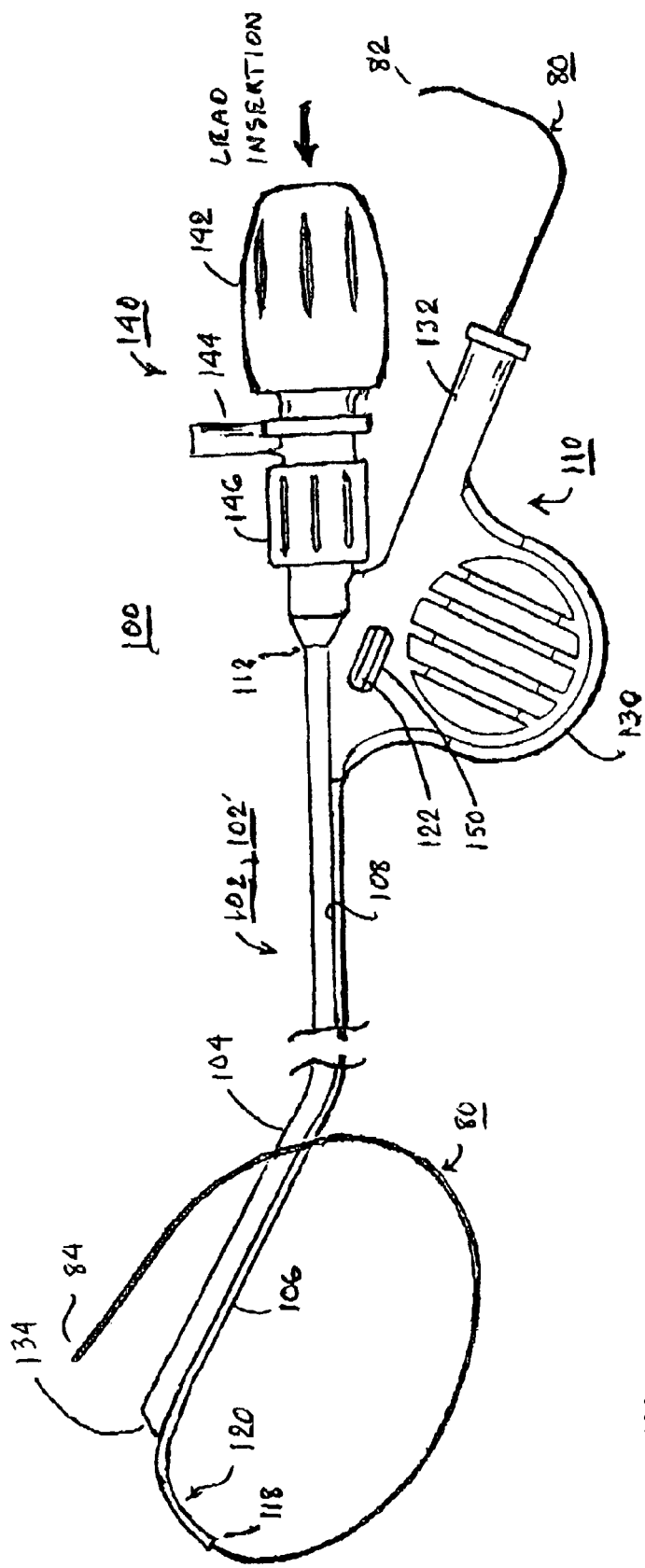
FIG. 5 is a plan view of a guidewire and an over-the-wire bilumen guide catheter adapted to be advanced through the tortuous pathway from outside the patient's body to the implantation sites illustrated in FIGS. 1 and 2, for example, over the guidewire.
Figure 6:
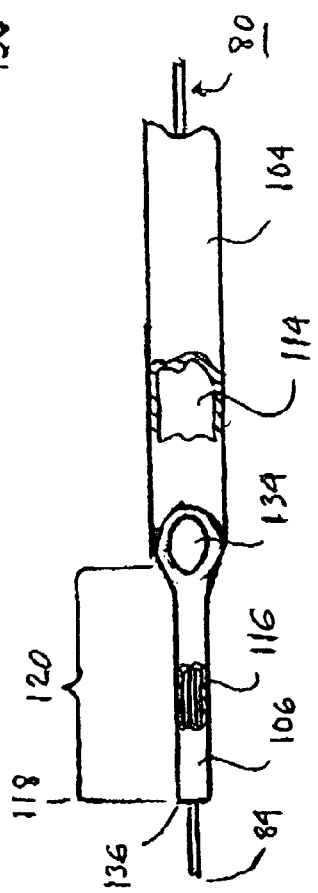
FIG. 6 is a partial view of a distal segment of the catheter body of FIG. 5 depicting the leader, the delivery lumen exit port, and the guidewire extending from the guide lumen exit port.

A first embodiment of an exemplary elongated bilumen guide catheter 100 adapted to be used with a guide tool such as a guidewire 80 is illustrated in FIGS. 5 and 6. The guidewire 80 extends between a guidewire proximal end 82 and a guidewire distal end 84 and is adapted to be advanced through the tortuous pathway from outside the patient's body to the implantation sites illustrated in FIGS. 1 and 2, for example. The bilumen guide catheter 100 is adapted to be advanced over the guidewire 80 through the same tortuous pathway to the illustrated implantation sites. The bilumen guide catheter 100 includes a relatively large diameter delivery lumen adapted to receive and introduce a small diameter cardiac lead, e.g., cardiac lead 10 through the tortuous pathway to dispose and fix the distal electrode 34 at an implantation site of the heart. The advancement is facilitated by advancement of a small diameter distal leader of the guide catheter 100 over the guidewire 80.

The bilumen guide catheter 100 includes an elongated catheter body 102 extending from a catheter body proximal end 112 joined with proximal handle or hub 110 to a catheter body distal end 118. The elongated catheter body 102 has a length of about 25 cm to 120 cm depending upon the length of the selected pathway from the skin incision through the patient's body to the implantation site. The catheter body 102 includes a delivery tube 104 joined to a guide tube 106 at the elongated junction 108. The delivery lumen 114 extends through the delivery tube 104, and the guide lumen 116 extends through the guide tube 106 in side-by-side relation. The delivery lumen 114 extends from a delivery lumen entry port 124 (shown in FIG. 10) through the length of delivery tube 104 to a delivery lumen exit port 134. The guide lumen 116 extends from a guide tube entry port 126 (shown in FIGS. 9 and 10) through the length of guide tube 106 to a guide lumen exit port 136 at the catheter body distal end 118. The delivery tube 104 is truncated at a point proximal to the catheter body distal end 118 to terminate the delivery lumen 114 and expose the delivery lumen exit port 134.

The catheter body 102 is thereby reduced in diameter and stiffness in the distal segment of the guide tube 106 extending between the delivery lumen exit port 134 and the guide lumen exit port 136 to form the flexible leader 120 adapted to readily track the guidewire 80 extending through the guide lumen 116. Consequently, the small diameter leader 120 can be advanced readily over guidewire 80 through twists and turns of the tortuous pathway and thereby guides the advance of the larger diameter proximal segment of the catheter body. The small diameter leader 120 can also be advanced deeply into narrow pathways or passages to dispose the more proximal delivery lumen exit port 134 at a desired implantation site.

Figure 9:
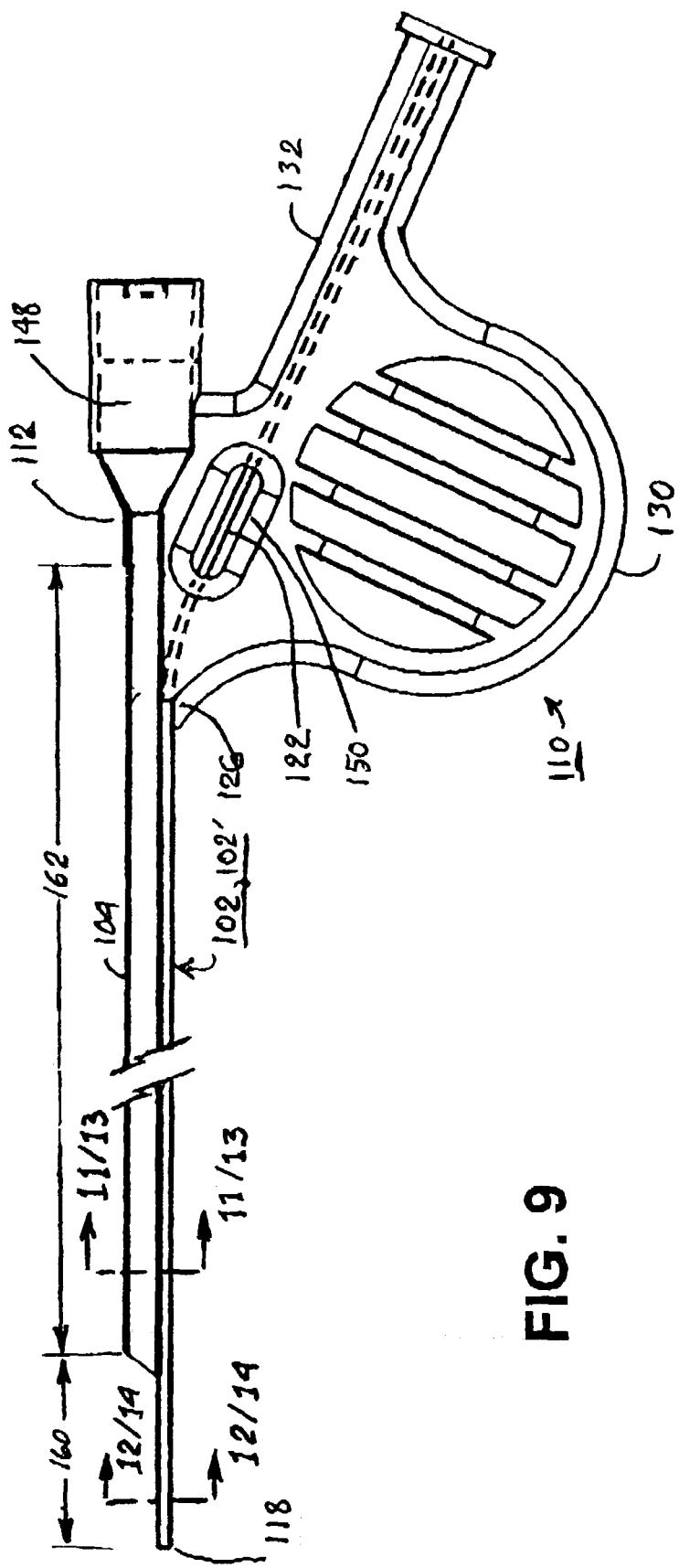
FIG. 9 is a plan view of the bilumen catheter body and hub of the bilumen guide catheters of FIGS. 5-8 illustrating the lead delivery lumen and guidewire or stylet lumen extending through the hub coupled to the catheter body proximal end.

In reference to FIG. 9, the distal leader 120 preferably has a length 160 on the order of approximately 10 mm to approximately 25 mm, and the length 162 of the catheter body 102 between the delivery lumen exit port 134 and the catheter body proximal end 112 is approximately 50 cm.

Figure 10:
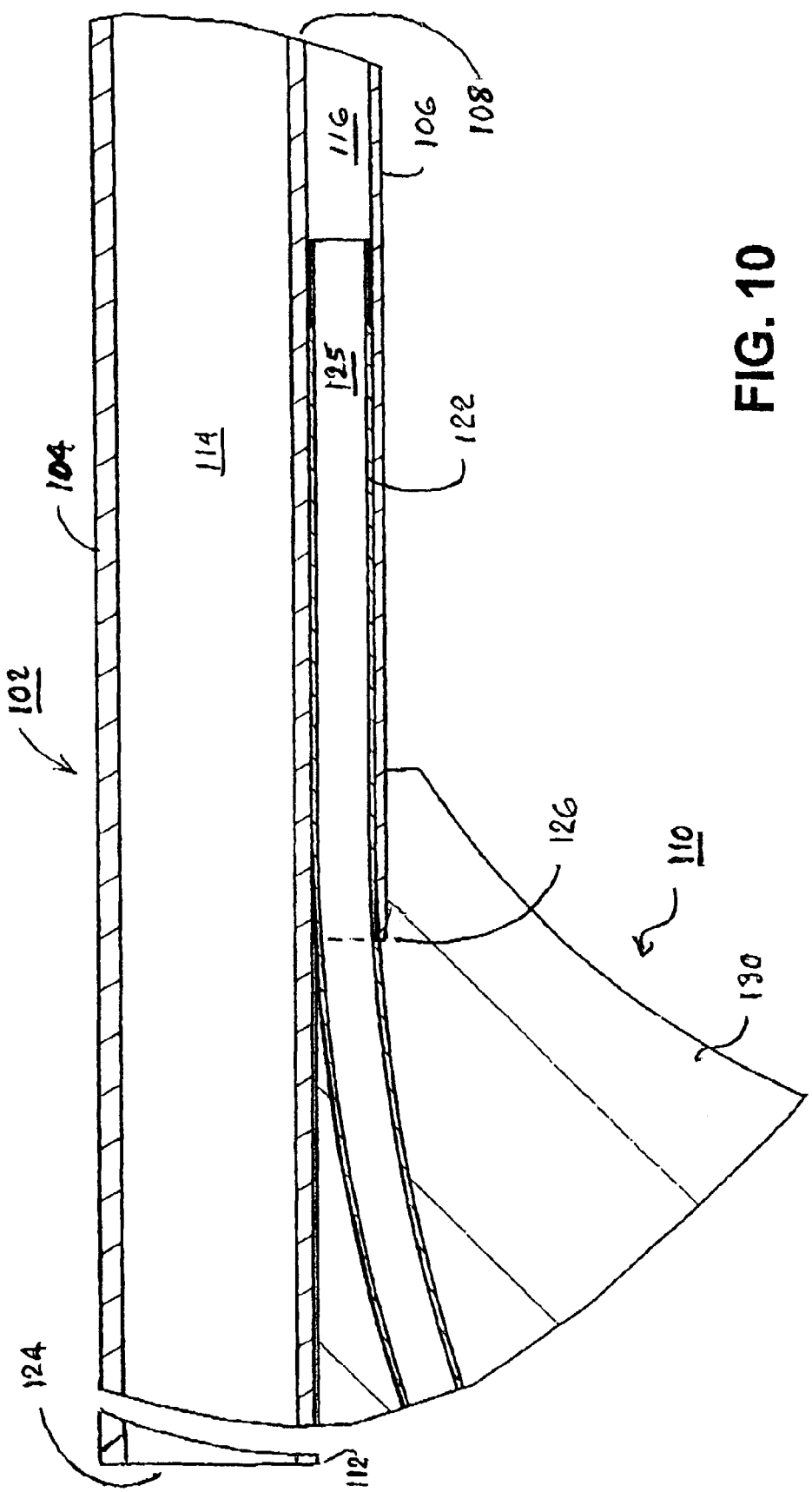
FIG. 10 is a partial cross-section view illustrating the mounting of the bilumen catheter body proximal end to the hub.

The hub 110 coupled to the guide catheter proximal end 112 is advantageously formed with a hub delivery lumen 148 axially aligned with the catheter body delivery lumen 114 and a hub guide lumen 125 defined by a hub guide tube 122 axially aligned with the guide lumen entry port 126 as shown in FIGS. 9 and 10. The hub 110 is shaped about the hub delivery lumen 148 to support a hemostasis valve 140 depicted in FIG. 7.

The hemostasis valve 140 includes a proximal rotating closure knob 142, an intermediate side port (extension hose and stopcock not shown) 144 and a distal rotating locking collar (for securing valve to luer hub fitting) 146 that is press fit onto the hub 110. The knob 142 and side port 144 and collar 146 are used in the fashion of a standard hemostasis valve manufactured by numerous suppliers to shut off the flow and to lock the lead or other catheter in relation to the catheter body. The valve 140 provides a lead insertion lumen axially aligned with the hub delivery lumen 148 so that a cardiac lead 10 of the types described above can be inserted therethrough and into the catheter body delivery lumen 114.

The hub guide tube 122 extends in an arcuate path through window 150 and the side extension 132 that can also be coupled with a Luer type hemostasis valve to seal around the guidewire 80 in a manner well known in the art. The hub 110 and the catheter body 102, particularly the delivery tube 104, are formed to be slittable along the lengths thereof to exposed the aligned hub lumen 148 and delivery lumen 114 to release the cardiac lead 60 introduced through the delivery lumen 114 in a manner described in the above-incorporated '346 and '433 patents. An enlarged, relatively flat pad or paddle 130 is formed extending away from the hub delivery lumen 148 and hub guide tube 122 that can be gripped on either side by the fingers to assist in holding and manipulating the hub 110 during adjustment of the valve 140 and advancement of the catheter body 102 through the tortuous pathway over the guidewire 80.

The guidewire 80 preferably has an outer diameter in the range of 0.025 inches (0.125 mm) to 0.045 inches (0.245 mm). The guidewire 80 can be a guidewire that is either introduced by itself or is introduced through a separate, small diameter introducer, e.g., a COOK® RoadRunner® Extra Support guidewire having an outer diameter of 0.018 inches (0.49 mm). The guidewire 80 can also be a deflectable or steerable guidewire of the type disclosed in commonly assigned U.S. Pat. No. 4,815,478, for example.

Figures 7, 8:
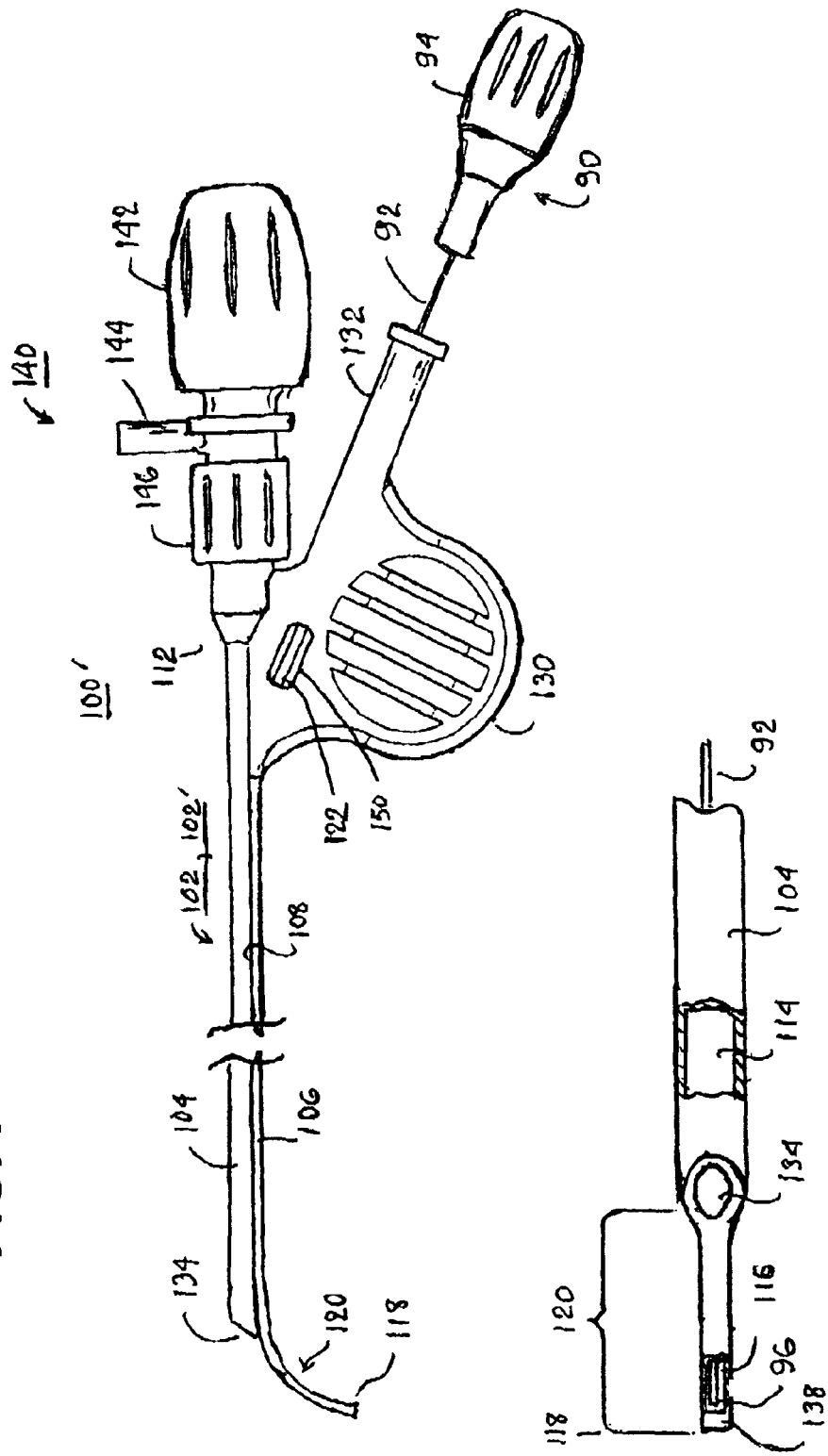
FIG. 7 is a plan view of a stylet and bilumen guide catheter adapted to be advanced through the tortuous pathway from outside the patient's body to the implantation sites illustrated in FIGS. 1 and 2, for example, with the stylet inserted into a stylet lumen.
FIG. 8 is a partial view of a distal segment of the catheter body of FIG. 7 depicting the leader, the delivery lumen exit port, and the stylet extending into the guide lumen within the leader.

The bilumen guide catheter 100 can also be advanced through the tortuous pathway employing a stiffening stylet substituted for guidewire 80 inserted into guide lumen to stiffen and selectively bend the distal leader 120 to during such advancement. Alternatively, a second embodiment of an exemplary elongated bilumen guide catheter 100 adapted to be used with a stylet 90 is illustrated in FIGS. 7 and 8. The bilumen guide catheter 100' is fabricated in substantially the same manner as the bilumen guide catheter 100 described above, except that the guide lumen exit port is preferably closed or blocked by a block 138 to inhibit the ingress of blood and fluids. The stylet 90 comprises a stainless steel wire 92 extending between a proximal stylet wire handle 94 and stylet wire distal end 96. The stylet wire 92 is adapted to be advanced through the hub guide lumen 125 and the catheter guide lumen 116 from outside the patient's body to abut the stylet distal end 96 against the blockage 138 at the catheter body distal end 118. The stylet wire 92 can have a stylet diameter of about 0.022 inches (0.55 mm). The stylet 90 can include a steerable stylet, e.g., the MEDTRONIC® Model 9210 steerable stylet or a steerable stylet of the types disclosed in commonly assigned U.S. Pat. Nos. 5,873,842 and 6,146,338.

Figure 11:
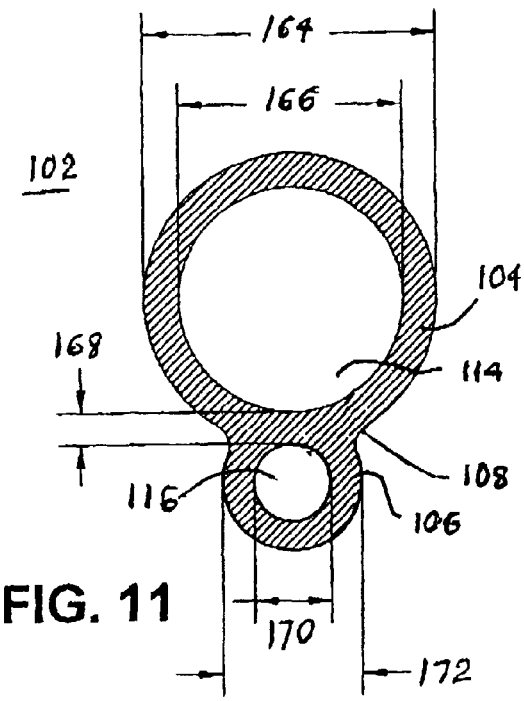
FIG. 11 is an end cross-section view taken along lines 11-11 in FIG. 9 proximal to the delivery lumen exit port of a first embodiment of the bilumen catheter body.
Figure 12:
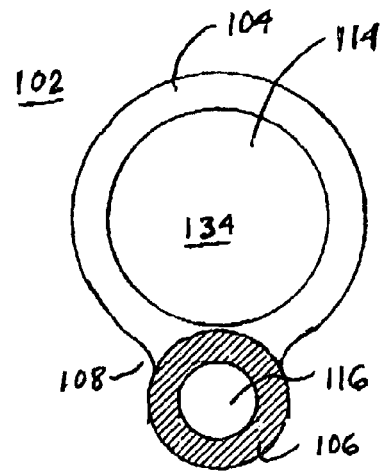
FIG. 12 is an end cross-section view taken along lines 12-12 in FIG. 9 distal to the delivery lumen exit port of the first embodiment of the bilumen catheter body.

The bilumen catheter body 102 can advantageously be formed by extrusion of a single polymeric material without the necessity of reinforcement or changing material characteristics along its length as shown in FIGS. 11 and 12. The bilumen catheter body 102 can be extruded from medical grade thermoplastic resins of 35D Shore durometer, for example, to form the delivery tube 104 joined to a guide tube 106 at the elongated junction 108. A radiopaque marker band can be incorporated at the at the catheter body distal end 118 at the distal tip of the distal leader 120.

In one example depicted in FIGS. 11 and 12, the delivery tube 104 has a delivery tube outer diameter 164 of approximately 1 French or 0.112 inches (2.79 mm), and the delivery lumen diameter 166 is approximately 0.086 inches (2.18 mm). The guide tube has a guide tube outer diameter 172 of approximately 0.054 inches (1.37 mm), and the guide lumen diameter 170 is approximately 0.030 inches (0.76 mm). The tube wall thickness is then equal to about 0.013 inches (0.33 mm).

Figure 13:
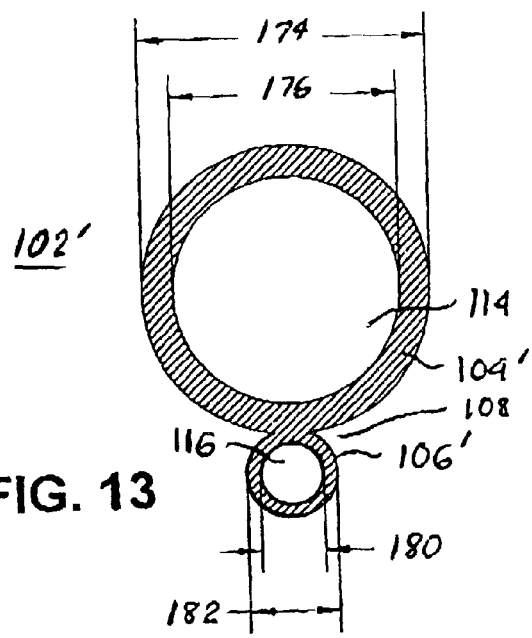
FIG. 13 is an end cross-section view taken along lines 13-13 in FIG. 9 proximal to the delivery lumen exit port of a second embodiment of the bilumen catheter body.
Figure 14:
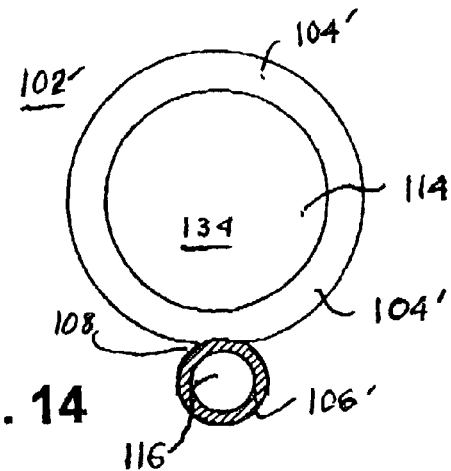
FIG. 14 is an end cross-section view taken along lines 14-14 in FIG. 9 distal to the delivery lumen exit port of the second embodiment of the bilumen catheter body.

A bilumen catheter body 102' can also advantageously be formed by co-extrusion of a two polymeric materials without the necessity of reinforcement or changing material characteristics along its length as shown in FIGS. 13 and 14. In a process of co-extruding tubing referred to as "paratubing", employed by PEXCO, Inc. Northborough, Mass., the delivery tube 104' defining the delivery lumen 114 is extruded of a medical grade thermoplastic resins having a first durometer, and the guide tube 106' defining the guide lumen 116 is extruded of a medical grade thermoplastic resins having a second durometer in a side-by-side extrusion process. The delivery tube 104' and the guide tube 106' are immediately brought together and adhered together to form the elongated junction 108. One or both of the delivery tube 104' and the guide tube 106' can be coated, at least in the area of the elongated junction 108, with a "tie-layer" of a tacky liquid polymer that aids in adhering the delivery tube 104' and the guide tube 106' together along the elongated junction 108.

The delivery tube 104' can be extruded from medical grade thermoplastic resins of 70D-75D Shore durometer, for example, and the guide tube 106' can be extruded from medical grade thermoplastic resins of 75A-35D Shore durometer, for example. The durometer of the delivery tube 104' is therefore lower than the durometer of the guide tube 106'. The higher durometer of the guide tube 106' enables guide tube 106' to be formed having a thinner wall than the wall of the delivery tube 104' so that the distal leader 120 can be made smaller in diameter while providing a suitable guide catheter lumen diameter to track a guidewire or to be directed into smaller diameter blood vessels or other body tracts. The harder surface of the higher durometer material tends to have lower contact stress and, thus, presents lower friction to the guidewire. Again, a radiopaque marker band can be incorporated at the catheter body distal end 118 at the distal tip of the distal leader 120.

One example of guide catheter body 102' formed by the paratubing process is depicted in FIGS. 13 and 14. The delivery tube 104 has a delivery tube outer diameter 174 of approximately 1 French or 0.112 inches (2.79 mm), and the delivery lumen diameter 176 is approximately 0.086 inches (2.18 mm). The guide tube 106' has a guide tube outer diameter 182 of approximately 0.034 inches (0.86 mm), and the guide lumen diameter 180 is approximately 0.024 inches (0.61 mm). The tube wall thickness is then equal to approximately 0.010 inches (0.25 mm). It should be noted that the guide lumen diameter 180 can be made the same as the delivery lumen diameter 176 to accept larger diameter stylets and guidewires.

The delivery tube 104 and guide tube 106 can be extruded from polyether block amide (PEBA), polyamide (PA), polyurethane (PU), polyester (PET), polybutylene terephthalate (PBT), or polyvinyl chloride (PVC). Optimally, the larger diameter delivery tube 104' can be co-extruded is extruded from one of the group consisting of PEBA, PU, PET or PVC having a relatively low durometer, whereas the smaller diameter guide tube 106' delivery tube is extruded from the group consisting of PEBA, PU, PA, PET, PBT or PVC having a relatively higher durometer. The tie-layer adhesive employed in the paratubing process can include a 0.003 inch (0.075 mm) layer of PU, PEBA, PA, PET, or PVC.

In both embodiments, the distal leader 120 is formed from the extrusion of the catheter body 102 or 102' by first cutting the extrusion into a length equal to length 160 plus length 162. The distal portion of the delivery tube 104 or 104' is cut away along the elongated junction 108 through the length 160 and at a bias angle to expose the delivery lumen exit port 134, leaving the distal portion of the catheter body 102 or 102' as the distal leader 120. Similarly, a proximal length of the guide tube 106 or 106' is cut away to fit the hub 110 and receive the hub guide tube 122 as shown in FIG. 10. The catheter body 102 or 102' is assembled with hub 110 to form the bilumen guide catheter 100 adapted to be introduced over the guidewire 80. The distal end opening of the guide lumen at catheter body distal end 118 is closed or blocked and the catheter body 102 or 102' is assembled with hub 110 to form the stylet guided bilumen guide catheter 100'.

In addition, an atraumatic soft tip can be applied at the catheter body distal end 118. The soft tip can be formed of a polyurethane, e.g., TECOFLEX® TT-1074A polyurethane sold by Thermedics Polymer Products, Inc., Woburn, Mass. The polyurethane material can be loaded with a radiopaque material, e.g. barium sulfate or tungsten powder, to make the resulting molded soft tip radiopaque.

Preferably, the surfaces of delivery lumen 114 and guide lumen 116 are coated with a lubricant to facilitate advancement of a cardiac lead 10 or other instrument through the delivery lumen 114 and the guidewire 80 or stylet wire 92 or other instrument through the guide lumen 116. The exterior surface of a distal portion of the bilumen catheter body 102 including the distal leader 120 can also be coated with the lubricant to facilitate advancement of the distal leader 120 through the tortuous pathway. Suitable biocompatible lubricating coatings include a silicone-based lubricant, e.g., a silicone oil, or a reactive silicone lubricant, e.g., MDX4-4159 silicone lubricant available from Dow Chemical Co., Midland, Mich. Other suitable biocompatible lubricating coatings include hydrophilic slip coating materials, e.g., polyacrylamide, polyvinylpyrrolidone, hyaluronic acid, or polyethylene oxide.

The bilumen guide catheters 100 and 100' can be employed in a variety of procedures for introducing cardiac leads into coronary veins of the heart, e.g., deep in the cardiac veins descending from the coronary sinus accessed transvenously and through the coronary sinus as illustrated in FIG. 2, to lodge the distal pace/sense electrode in relation to the left ventricle. The guide catheters 100 and 100' can also be employed to fix a pace/sense electrode at particular sites in a heart chamber, e.g., the right ventricular outflow tract, as illustrated schematically in FIG. 20, for example.

In another approach, the guide catheters 100 and 100' can be used to implant a cardiac lead in the right atrial wall adjacent to the ostium of the coronary sinus to locate the distal pace/sense electrode in optimal relation to the Bundle of His or in a portion of the right atrium known as the "triangle of Koch". The triangle of Koch is a portion of the right atrial wall, containing the AV node, limited distally by the septal attachment of the tricuspid valve and proximally by the sinus septum, and adjacent to the ostium of the coronary sinus. Cardiac potential mapping studies have shown that the triangle of Koch frequently exhibits double spiked and fractionated electrograms and may be subject to reduced conduction speed and that cardiac pacing in the triangle of Koch can be beneficial as described in commonly assigned U.S. Pat. No. 5,403,356.

It is necessary to carefully locate the implantation site and to fix the distal pace/sense electrode(s) at the implantation site to prevent inadvertent perforation and dislodgement. Accessing these sites of the right atrium can be difficult employing conventional stiffening stylets inserted into a cardiac lead lumen for stiffening the lead body and steering the distal fixation mechanism to the implantation site.

Figure 15:
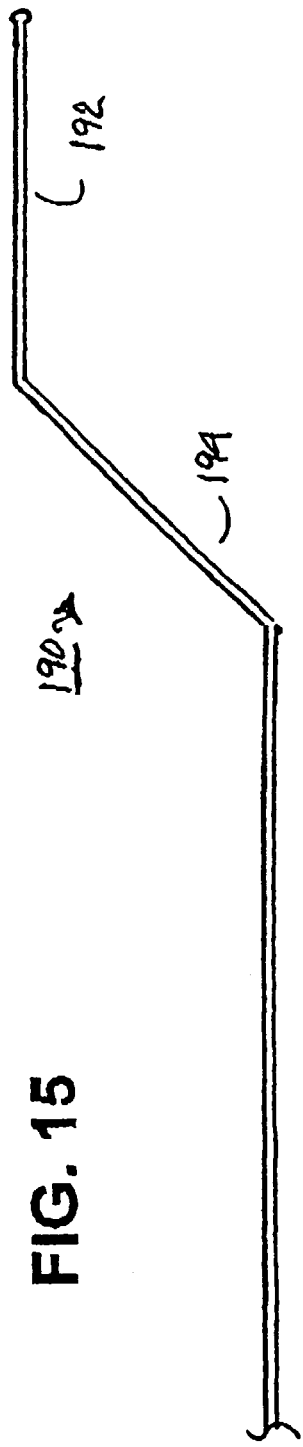
FIG. 15 is a view of the distal portion of the guide catheter of FIG. 5 employing a shaped stylet for accessing the coronary sinus to dispose a distal fixation helix of the cardiac lead of FIG. 3 at an implantation site within the right atrium adjacent to the Bundle of His.
Figure 16:
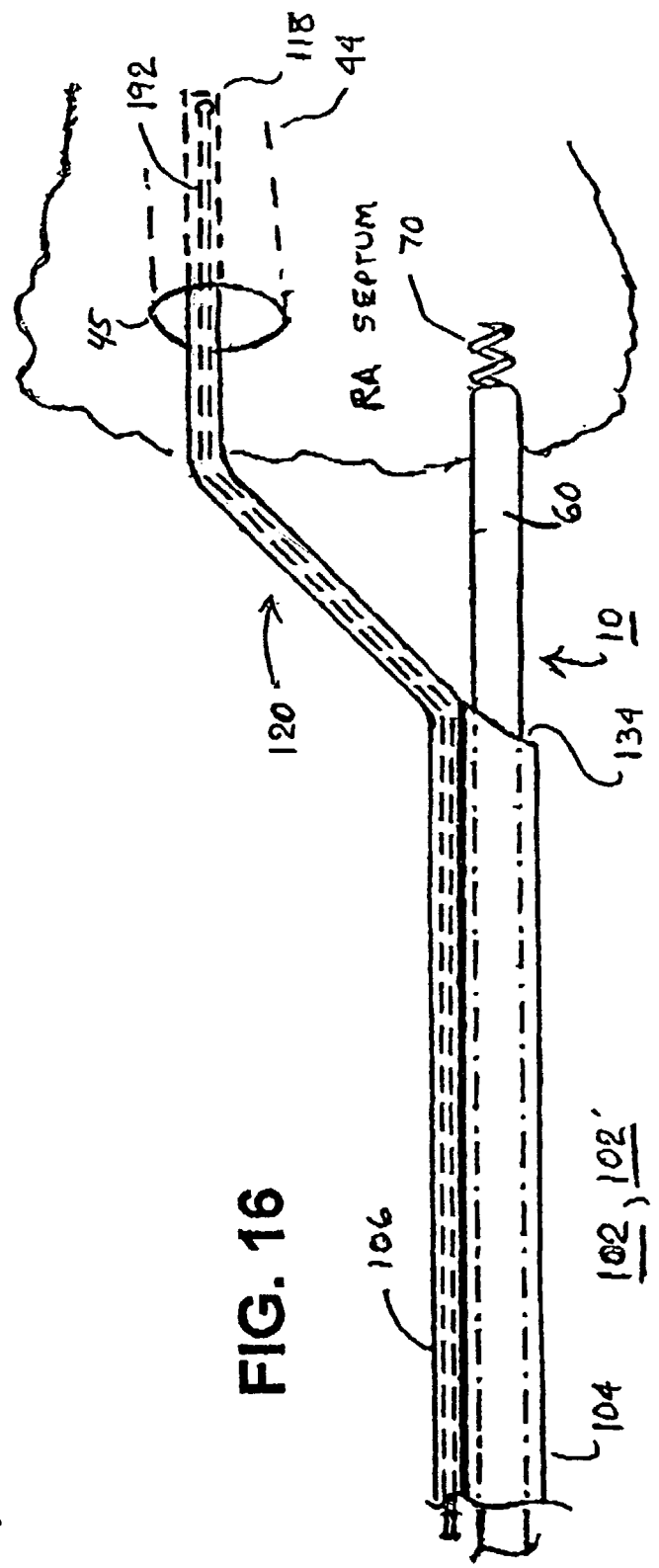
FIG. 16 is a view of the shaped stylet employed in accessing the coronary sinus as illustrated in FIG. 15.

Advantageously, the guide catheter 100' can be employed to locate the distal leader 120 within the ostium of the coronary sinus. In particular, a first stylet 90 of the types described above is inserted into the guide lumen 116 to advance the bilumen guide catheter 100' into the right atrium with the cardiac lead 10 loaded in the delivery lumen 114. The first stylet 90 is removed from the guide lumen and a second stylet 190 having a distinct step 194 in the distal segment of the stylet wire 192 as shown in FIG. 15 is fitted through the hub guide lumen 125 formed by the hub guide tube 122 at the end of extension 132 and advanced through the guide lumen 116 of the guide tube 106 or 106' to locate the step in the distal segment of the stylet wire 192 within the guide lumen 116 within the distal leader 120 to laterally offset the distal end of the leader with respect to the delivery lumen exit port 134. The offset distal end of the leader 120 can then be advanced into the ostium 45 of the coronary sinus 44 as shown in FIG. 16. The delivery lumen exit port 134 is then oriented to the desired implantation site along the RA septum. The catheter body 102 or 102' can be rotated somewhat about the distal leader 120 disposed in the ostium to sweep the distal fixation helix to a desired implantation site. The distal fixation helix 70 of the cardiac lead 10 can then be screwed into the atrial septum in optimal relation to the bundle of His or a desired location in the triangle of Koch.

The following procedures for visualizing the coronary vessels, particularly coronary veins branching from the coronary sinus, can advantageously be practiced using the same bilumen catheters 100 and 100' that are then used to implant a cardiac lead 10 as described above.

Figure 17:
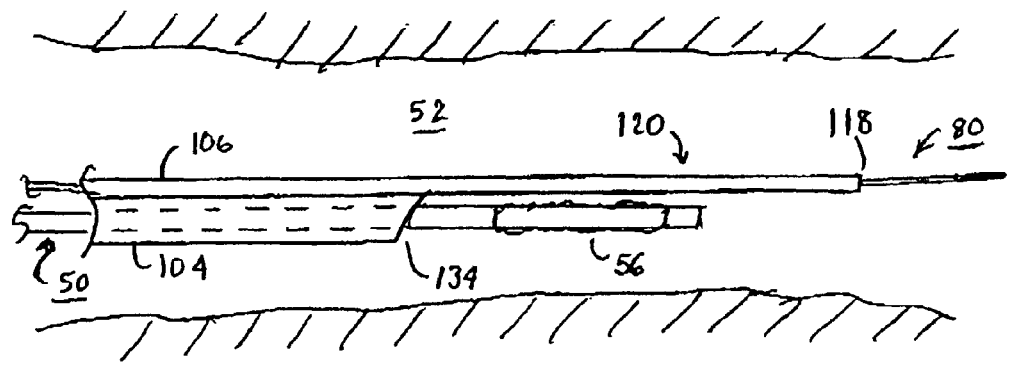
FIG. 17 is a view of the distal portion of the guide catheter of FIG. 5 advanced into a cardiac vessel and the introduction of a deflated balloon of a balloon catheter introduced into the cardiac vessel through the lead delivery lumen.
Figure 18:
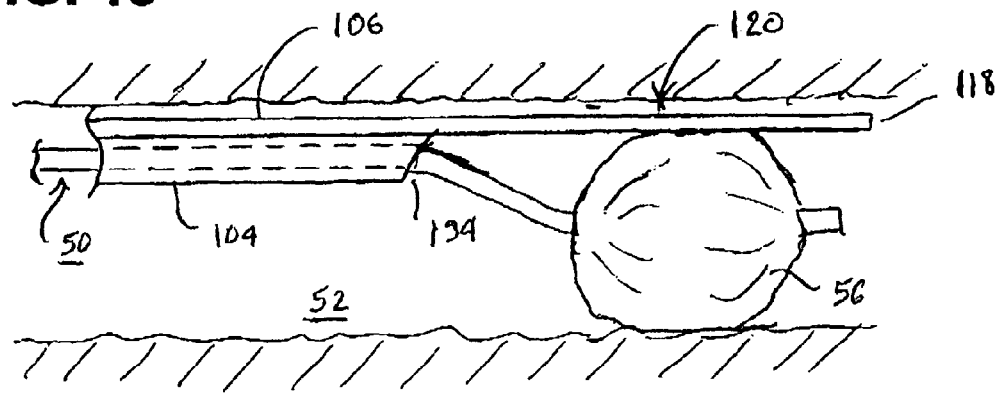
FIG. 18 is a view the distal portion of the guide catheter of FIG. 5 advanced into a cardiac vessel and the inflation of the balloon of a balloon catheter introduced through the lead delivery lumen to obstruct the cardiac vessel.
Figure 19:
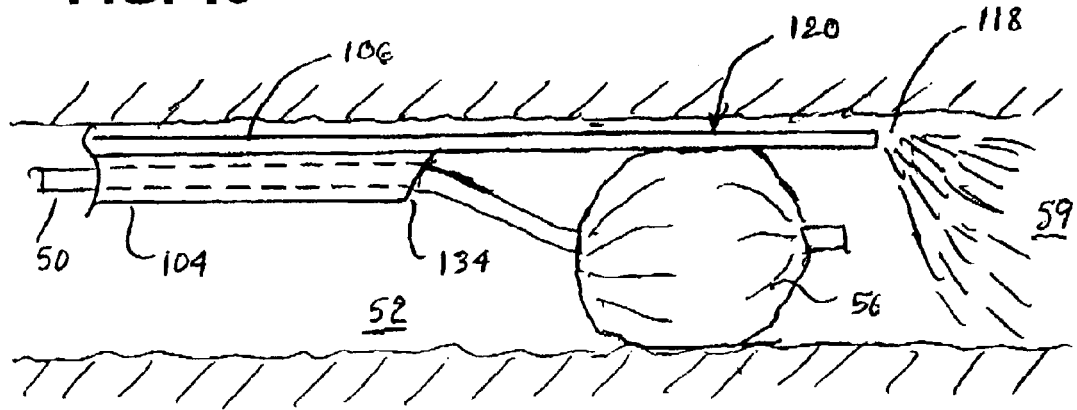
FIG. 19 is a view of the passage of contrast agent through the guide lumen and into the cardiac vessel distal to the inflated balloon.

The bilumen guide catheter 100 can advantageously be used to perform other functions, e.g., to facilitate blocking of a cardiac vessel or other body tract lumen 52 employing a balloon catheter 50 so that radiopaque diagnostic fluid 54 can be introduced into the cardiac vessel lumen to visualize the cardiac vessel in an angiographic procedure in order to identify a suitable implantation site as shown in FIGS. 17-19. In particular, a stylet 90 of the types described above is inserted into the guide lumen 116 to advance the bilumen guide catheter 100' into the vessel or other tract lumen 52. Or, the bilumen guide catheter 100 is introduced over a guidewire 80 as shown in FIG. 17 to advance the distal leader 120 and delivery lumen exit port 134 to the particular site of the blood vessel to be visualized under fluoroscopy.

A balloon catheter or guidewire, e.g., a MEDTRONIC® Model 6215 occluding balloon catheter, is advanced through the delivery lumen 114 and out of the delivery lumen exit port 134 in FIG. 17. The balloon 56 of the balloon catheter 50 is inflated in FIG. 18 to substantially block fluid flow past the inflated balloon 56, and the guidewire 80 (or stylet 90) is withdrawn from the guide lumen 116. Then, radiographic fluid 59 is injected through the guide lumen 116 into the vessel or tract lumen 52 as shown in FIG. 18 to outline the vasculature distal to the inflated balloon 56.

Alternatively, the bilumen catheter 100' can be employed in the process illustrated in FIGS. 17-19 so that the catheter body distal end 118 is located at the site in the cardiac vessel using the stylet 90 rather than over-the-wire using the guidewire 80 depicted in FIG. 17. The balloon catheter 50 is inserted and the balloon 56 is inflated as shown in FIG. 18. However, the radiographic fluid 59 is delivered into the vessel lumen 52 distal to the inflated balloon 56 through a lumen of the balloon catheter 50.

In a still further embodiment, an inflatable balloon could be added to the end of the leader 120 of the bilumen guide catheter 100' that is inflated or deflated through the guide lumen 116. The balloon could be used to anchor the catheter body distal end 118 and be used to occlude the vessel lumen 59 to facilitate a venogram, that is, a fluoroscopic image of vein structures filled with contrast agent.

The bilumen guide catheters 100 and 100' can be downsized to access to short, rather narrow tracts, e.g., the urinary tract or for accessing the brain by way of the arteries and veins (preferably the veins) for neurovascular procedures.

Figure 20:
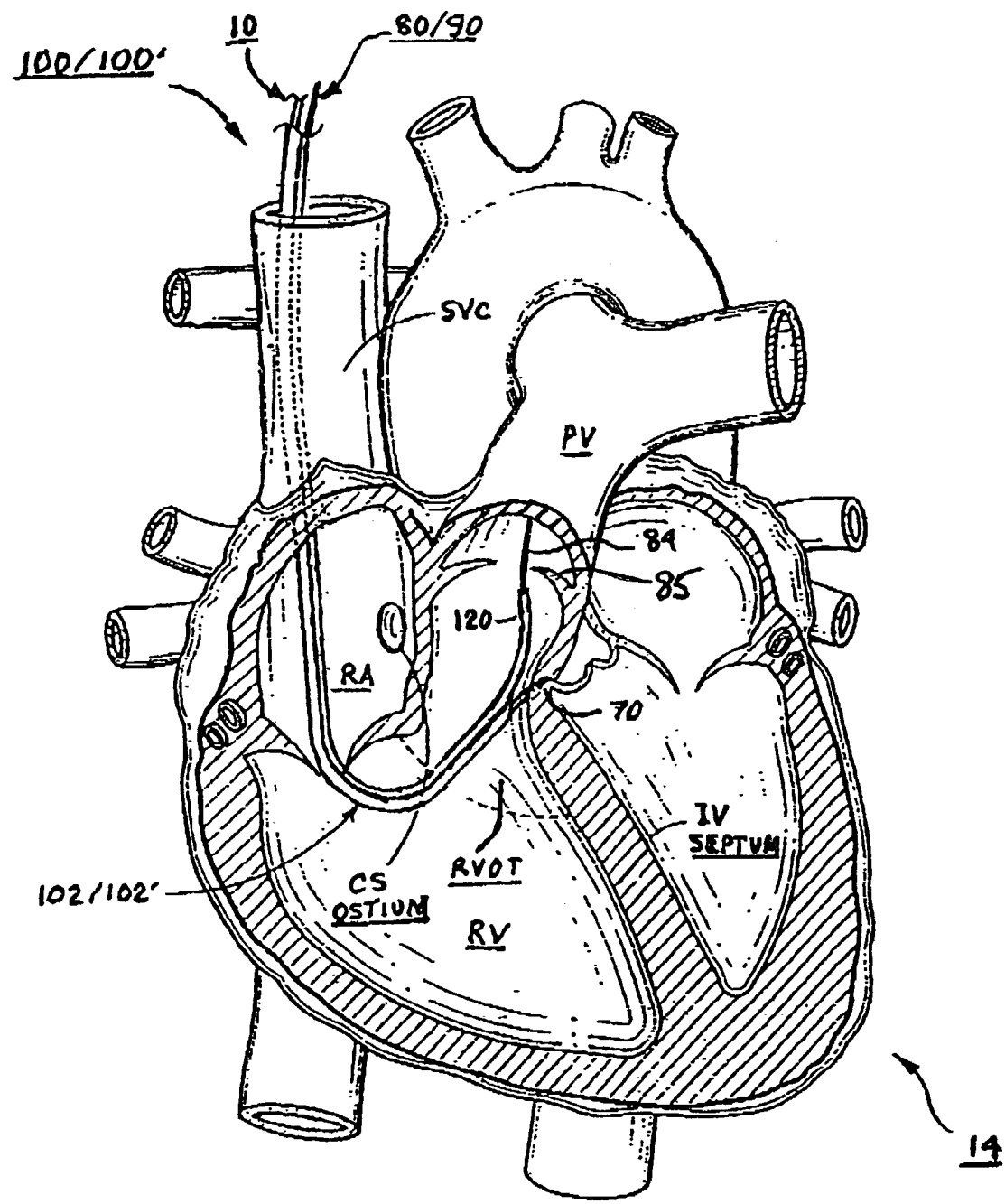
FIG. 20 is a schematic representation of the advancement of a fixation mechanism of a cardiac lead to an implantation site of the right ventricular outflow tract.

A particular use of the bilumen guide catheters 100, 100' to implant a cardiac lead 60 in the interventricular septum (IV SEPTUM) separating the RV from the LV within the left ventricular outflow tract (LVOT) is depicted schematically in FIG. 20. In this example, the catheter body 102/102' is guided over a guidewire 80 or stylet 90 so that the distal leader 120 extends toward or through the pulmonary valve 85. Use of a guidewire 80 is particularly advantageous because the guidewire distal end 84 can be advanced as deeply as desired into the pulmonary vein (PV) to maintain the leader 120 oriented toward or extending through the pulmonary valve 85.

The lead 60 can be preloaded into the delivery lumen so that the distal fixation mechanism 70 is advanced from the delivery lumen exit port and screwed into the IV SEPTUM once the delivery lumen exit port is at the desired implantation site. The particular implantation site in the IV SEPTUM can be selected by moving the distal leader 120 along the guidewire 80 or stylet 90. Moreover, the catheter body 102/102' can be rotated about the guidewire 80 to orient the delivery lumen exit port around the LVOT to any desired implantation site close to the pulmonary valve PV and the atria.

CONCLUSION

All patents and publications identified herein are incorporated herein by reference in their entireties.

While particular embodiments of the invention have been disclosed herein in detail, this has been done for the purposes of illustration only, and is not intended to limit the scope of the invention as defined in the claims that follow. It is to be understood that various substitutions, alterations, or modifications can be made to the disclosed embodiments without departing from the spirit and scope of the claims. The above described implementations are simply those presently preferred or contemplated by the inventors, and are not to be taken as limiting the present invention to the disclosed embodiments. It is therefore to be understood, that within the scope of the appended claims, the invention may be practiced otherwise than as specifically described without actually departing from the spirit and scope of the present invention.

The invention claimed is:

1. A bilumen catheter, comprising:
a delivery tube comprised of a first polymeric material having a first durometer and having a delivery tube outer wall and a delivery tube inner wall forming a delivery tube lumen; and
a guide tube having a guide tube outer wall and a guide tube inner wall forming a guide tube lumen,
the guide tube outer wall having a length fixedly bonded to the delivery tube outer wall in a side-by-side manner forming an elongated junction between the guide tube outer wall and the delivery tube outer wall along the length of the guide tube, the length of the guide tube comprised of a second polymeric material having a second durometer, the second durometer greater than the first durometer of the first polymeric material,
the guide tube having a harder surface than the delivery tube.

2. The bilumen catheter of claim 1, further comprising:
a proximal hub forming a hub delivery lumen in fluid communication with the lumen of the delivery tube at the delivery tube proximal end and a hub guide lumen in fluid communication with the lumen of the guide tube at the guide tube proximal end.

3. The bilumen catheter of claim 2, wherein the hub and the delivery tube are formed to be slittable.

4. A bilumen guide catheter for introducing a cardiac lead to a desired implantation site, comprising:
an elongated delivery tube, formed from a first polymeric material having a first durometer, extending from a delivery tube proximal end to a delivery tube distal end and having a delivery tube inner wall spaced a first distance from a delivery tube outer wall, the delivery tube inner wall forming a delivery tube lumen and the delivery tube lumen having an exit port at the delivery tube distal end; and
an elongated guide tube having a length, the length of the guide tube formed from a second polymeric material different from the first polymeric material and having a second durometer greater than the first durometer of the first polymeric material, extending from a guide tube proximal end to a guide tube distal end and having a guide lumen inner wall spaced a second distance from a guide tube outer wall, the guide tube inner wall forming a guide tube lumen having a guide tube lumen exit port at the guide tube distal end, the guide tube outer wall fixedly bonded against the delivery tube outer wall, wherein the distal end of the guide tube is positioned distally from the distal end of the delivery tube,
the guide tube having a harder surface than the delivery tube.

5. The bilumen guide catheter of claim 4 wherein a wall thickness of the elongated delivery tube is at least twice a wall thickness of the elongated guide tube.

6. The bilumen guide catheter of claim 5 wherein an outer diameter of the delivery tube is at least twice an outer diameter of the elongated guide tube.

7. The bilumen guide catheter of claim 1 wherein the first polymeric material is selected from a group consisting of polyether block amide, polyurethane, polyester, and polyvinyl chloride, and wherein the second polymeric material is selected from a group consisting of polyether block amide, polyurethane, polyamide, polyester, polybutylene terephthalate, and polyvinyl chloride.

8. The bilumen catheter of claim 1 wherein
the delivery tube is truncated at a delivery lumen exit port proximal to a distal end of the catheter,
the guide tube forms a leader extending between the delivery lumen exit port and the distal end of the catheter,
the leader having a length of at least approximately 10 mm.

9. The bilumen catheter of claim 1 wherein
the delivery tube is truncated at a delivery lumen exit port proximal to a distal end of the catheter,
the guide tube comprising a leader extending between the delivery lumen exit port and the distal end of the catheter, the guide tube leader comprising the second material having the second durometer greater than the first durometer.

* * * * *